(12) United States Patent
Hilmer et al.

(10) Patent No.: US 6,703,218 B2
(45) Date of Patent: Mar. 9, 2004

(54) PROCESS FOR THE PREPARATION OF LINALOOL OXIDE OR OF LINALOOL OXIDE-CONTAINING MIXTURES

(75) Inventors: Jens-Michael Hilmer, Höxter (DE); Ian-Lucas Gatfield, Höxter (DE)

(73) Assignee: Haarman & Reimer GmbH (DE)

( * ) Notice: Subject to any disclaimer, the term of this patent is extended or adjusted under 35 U.S.C. 154(b) by 0 days.

(21) Appl. No.: 10/000,426

(22) Filed: Nov. 2, 2001

(65) Prior Publication Data

US 2002/0086376 A1 Jul. 4, 2002

(30) Foreign Application Priority Data

Nov. 7, 2000 (DE) .......................... 100 55 092

(51) Int. Cl.$^7$ .............................. C12P 1/00; C12N 9/20
(52) U.S. Cl. .......................................... 435/41; 435/198
(58) Field of Search ..................... 435/198, 41

(56) References Cited

FOREIGN PATENT DOCUMENTS

| JP | 59-225176 | 12/1984 |
|---|---|---|
| WO | 91/04333 | 4/1991 |

OTHER PUBLICATIONS

Common Fragrance and Flavor Materials, 2$^{nd}$ ed. (month unavailable) 1990, p. 114, Kurt Bauer, Dorothea Garbe, Horst Surburg, "Single Fragrance and Flavor Compounds".
Med. Fac. Landbouwkd. Toegepaste Biol Wet. 36/4a (month unavailable) 1998, pp. 1321–1324. J.C.R. Demyttenaere, "Biotransformation of Terpenes by Fungi for the Production of Bioflavours".
Phytochemistry, 47 (6), (month unavailable) 1998, pp. 1029–1036, Jan C. R. Demyttenaere and.
Chem. Commun. (month unavailable) 1998, pp. 177–178, Ann W.P. Jarvie, Nigel Overton and Christopher B. St. Pourcain, "Enzymatic expoxidation of polybutadiene".
J. Chem. Soc. Erkin Trans I, (month unavailable) 1995, pp. 89–91, Stephanie C. Lemoult, Paul F. Richardson and Stanley M. Roberts, "Lipase–catalysed Baeyer–Villiger Reactions".
Lipid Technology, Jul. 1996, pp. 77–80, Mark Rüsch gen. Klaas and Siegfried Warwel, "Peroxy fatty acids: lipase–catalysed preparation and expoxidation".
Biotechnology Letters, vol. 19, No. 7, Jul. 1997, pp. 611–613, Yuki Miura and Tsuneo Yamane, "Epoxidation of alkanes and cycloalkanes by microbial lipases immobilizaed with photo–crosslinkable resin prepolymer".
Niku–Paavola, M –L et al: "Enzymatic oxidation of alkenes." Journal of Molecular Catalysis B Enzymatic, Bd. 10, Nr. 4, Sep. 18, 2000, Seiten 435–444, XP002191960 ISSN: 1381–1177 * Absatz '03.1!; Tabelle 1*.
Mischitaz, M., Faber, K.: "Chemo–enzymatic synthesis of (2R,5S)– and (2R,5R)–5–(1–hydroxy–1–methylethyl)–2–methyl–2– vinyl––tretrahydrofuan ('Linalool Oxide'): preparative applications of a highly selective bacterial epoxide hydrolase" Synlett, 1996, Seiten 978–980, XP002191961 *das ganze Dokument *.
Franssen M C R et al: "Enzymatic Alcoholysis of Alkoxymethyl Alkanoates: a Possible Approach for the Kinetic Resolution of Tertiary Alcohols" Tetrahedron Letters, Elsevier Science Publishers, Amsterdam, NL, kBd. 39, Nr. 45, Nov. 5, 1998, Seiten 8345–8348, XP004139413 ISSN: 0040–4039 scheme 2, compounds 4b and 2b. Seite 8348,, * Zeile 8—Zeile 9; Abbildung 3 *.
David L et al: "Oxidative Cyclization of Linalol by Various Microorganisms" Agricultural and Biological Chemistry, Bd. 49, Nr. 5, 1985, Seiten 1487–1489, XP002191962 ISSN: 0002–1369 * das ganze Dokument *.
Demyttenaere et al., Phytochemistry, vol. 47, No. 6, pp. 1029–1036, 1998.

*Primary Examiner*—Michael Meller
(74) *Attorney, Agent, or Firm*—Pendorf & Cutliff

(57) ABSTRACT

The present invention relates to a process for the preparation of linalool oxide or of linalool oxide-containing mixtures, in which linalool or linalool-containing mixtures are oxidized in the presence of enzymes.

7 Claims, No Drawings

US 6,703,218 B2

PROCESS FOR THE PREPARATION OF LINALOOL OXIDE OR OF LINALOOL OXIDE-CONTAINING MIXTURES

FIELD OF THE INVENTION

The present invention relates to a process for the preparation of linalool oxide or of linalool oxide-containing mixtures.

BACKGROUND OF THE INVENTION

Linalool oxide is an aroma material, which has been known for a long time and is used in a large number of aromas. Linalool oxide, moreover, occurs both in the furanoid form as a nine-membered ring (2-methyl-2-vinyl-5-(α-hydroxyisopropyl)tetrahydrofuran, CAS 60047-17-8; cis and trans: CAS 5989-33-3 and 34995-77-2), and in the pyranoid form as 6-membered ring (2,2,6-trimethyl-6-vinyltetrahydro-2H-pyran-3-ol, CAS 14049-11-7; cis and trans: CAS 14009-71-3 and 39028-58-5). It occurs naturally in essential oils such as rosewood oil and osmanthus abs. and fruits (Volatile Compounds in Food, Qualitative and Quantitative Data, 7th edition, 1996, TNO Nutrition and Food Research Institute, Zeist, the Netherlands) and has as a flowery-earthy, slightly bergamot-like odor (Bauer, Garbe, Surburg, Common Fragrance and Flavor Materials, second edition, VCH, Weinheim 1990, p. 114). The flavor impression of linalool oxide is in the citrus, apricot, blueberry, flowery direction.

The person skilled in the aroma sector distinguishes three areas: natural, nature-identical and synthetic aromas. Synthetic aromas are of only minor interest because consumer acceptance is not particularly high. One example of the preparation of a nature-identical aroma material is described in JP A 59225176. This publication relates to the production of linalool oxide. In this case, unnatural starting materials are converted by chemical synthesis using strong mineral acids into linalool oxide. Such a product can be categorized only as "nature-identical", but not as natural, and must, therefore, not be used to produce natural aromas.

Natural aromas, and thus also the natural aroma materials present therein, are to be categorized as having the highest value. This is also shown clearly by the considerably higher prices, which can be obtained for natural aromas. In addition, consumer interest in natural products and thus, also in natural aromas required for their production is increasing.

It is therefore an aim of the aroma industry to have natural building blocks for natural aromas available in sufficient quantity and quality. However, it is usually not economical to isolate these individual building blocks from natural extracts.

One example of the production of linalool oxide by fermentation is disclosed by *Demyttenaere* (Demyttenaere, J. C. R., 1998, Biotransformation of terpenes by fungi for the production of bioflavors, Meded.—Fac. Landbouwkd. Toegepaste Biol. Wet., 63 (4a), 1321–1324, and Demyttenaere, J. C. R.; Willemen, H. M., 1998, Biotransformation of linalool to furanoid and pyranoid linalool oxides by *Aspergillus niger*, Phytochemistry, 47 (6), 1029–1036). The biotransformation of terpene alcohols with the aid of *Aspergillus niger* and Penicillium strains is described therein. However, this process is very complicated to carry out, the conversion is very slow, and the yields of linalool oxide are only 20–33%.

In addition, the use of enzymes for epoxidation of double bonds in fatty acids and alkenes is known (1. PCT WO 91/04333. 2. Jarvie, A. W. P.; Overton, N.; St. Pourcain, C. B., 1998, Enzymatic epoxidation of polybutadiene, Chem. Comm., 177–178. 3. Lemoult, S. C.; Richardson, P. F.; Roberts, S. M., 1995, Lipase catalyzed Baeyer-Villiger Reactions, J. Chem. Soc. Perkin Trans. I, 89–91. 4. Rüsch, M.; Warwel, S., 1996, Peroxy fatty acids: lipase catalyzed preparation and epoxidation, Lipid Technology, 7, 77–80. 5. Miurra, Y.; Yamane, T., 1997, Epoxidation of alkanes and cycloalkanes by microbial lipases immobilized with photo crosslinkable resin prepolymer, Biotechnol. Lett., 19, 7, 611–613). This involves epoxidation of double bonds analogous to the chemical reaction with a peroxycarboxylic acid. In these cases, the enzyme lipase (E. C. 3.1.1.3, CAS No. 9001-62-1, for example from *Pseudomonas cepacia*, DSM 3959, *Candida antarctica* DSM 3855, DSM 3908, DSM 3909*Mucor mieh, Humicola lanuginosa*, DSM 3819, DSM 4109, *Humicola brevispora*, DSM 4110, *Humicola brevis* var. *thermoidea*, DSM 4111, *Humicola isolens*, DSM 1800) catalyzes, in the presence of hydrogen peroxide, intermediate formation of the peroxycarboxylic acid (WO 91/04333).

Numerous publications disclose the use of lipases on the laboratory or manufacturing scale, essentially for esterifications or transesterifications. However, none of these descriptions describes the preparation of furanoid or pyranoid linalool oxide by an enzymatic route.

SUMMARY OF THE PRESENT INVENTION

It is an object of the present invention now to produce linalool oxide or a linalool oxide-containing mixture, which can be categorized as natural and can be used to produce natural aromas. An additional aim is for the yields to be distinctly higher than in the state of the art to date. A particular aim is to achieve yields above 90%.

A process for the preparation of linalool oxide or of linalool oxide-containing mixtures has been found and is characterized in that linalool or linalool-containing mixtures are oxidized in the presence of an enzyme.

DETAILED DESCRIPTION OF THE INVENTION

It is possible to use in the process according to the present invention both D-linalool and L-linalool. These substances may be in pure form or in the form of a mixture. It is likewise possible to employ the linalools mixed with other substances.

Suitable other substances are essential oils, absolutes or extracts. In a preferred embodiment, linalool can be present in the essential oils such as rosewood oil, coriander oil, basil oil, lavender oil etc. It is also possible in these cases for D-linalool or L-linalool to be present as single substances in the reaction medium. A mixture of D-linalool and L-linalool in the reaction medium is, of course, likewise suitable for the purposes according to the present invention.

The enzymes employed according to the present invention are preferably hydrolases, specifically lipases or proteases. Lipases are suitable and particularly preferred according to the present invention. In particular, a mobilized lipase is preferred, for example Chirazym C2 L2 from Roche Diagnostics, Penzberg, Germany, or Novozym 435 from Novo Nordisk, Denmark.

The enzymes are preferably those which can be obtained with the aid of the following microorganisms: *Pseudomonas cepacia*, for example DSM 3959, *Candida antarctica*, for example DSM 3855, DSM 3908, DSM 3909*Mucor mieh, Humicola lanuginosa*, for example DSM 3819, DSM 4109,

*Humicola brevispora*, for example DSM 4110, *Humicola brevis var. thermoidea*, for example DSM 4111, *Humicola isolens*, for example DSM 1800.

Yeasts are preferred as enzyme producers. Candida species in the form of pure cultures or mixed cultures of these yeasts are more preferred for this purpose, especially the *Candida antarctica*. Accordingly, lipases from *Candida antarctica* are most preferred for the process according to the present invention.

In the process according to the present invention, the oxidation of linalool was preferably carried out in the presence of said enzymes and of an oxidizing agent. Hydrogen peroxide is preferred. The oxidizing agent can be added before or during the oxidation process. It is likewise possible according to the present invention for the medium to have such a composition and/or for the reaction conditions to be chosen such that the required oxidizing agent is formed during the progress of the process according to the present invention. In particular, the formation of oxidizing agent can be carried out with the use of enzymes. Examples thereof, are oxidases, for example, glucose oxidase. It is also possible to use as non-enzymatic catalysts for preparing the hydrogen peroxide.

It is, thus, possible in the variant according to the present invention, for example, to choose the combination of the medium and of the enzymes such that the hydrogen peroxide is produced in situ during the process. This may involve the hydrogen peroxide production being started before the oxidation process begins, or the hydrogen peroxide production being allowed to take place in situ during the oxidation process. It is possible according to the present invention, for example, for the hydrogen peroxide to be formed enzymatically by oxidizing glucose in the aqueous medium with the enzyme glucose oxidase.

In addition to the use of enzymes and oxidizing agents it is often also possible to add a solvent to the reaction solution. Solvents suitable according to the present invention are acidic esters, preferably ethyl acetate. Apart from the esters, also suitable are carboxylic acids able to form peroxycarboxylic acids. Examples thereof, are acetic acid, formic acid, benzoic acid. Acetic acid is more preferred.

The preferred solvents according to the present invention are those able to form peracids with the aid of the enzymes in the presence of hydrogen peroxide. One example, thereof, is ethyl acetate which forms peracetic acid as an intermediate in the presence of hydrogen peroxide with the aid of lipases.

In a form, which is particularly preferred according to the present invention, the following reaction accordingly takes place:

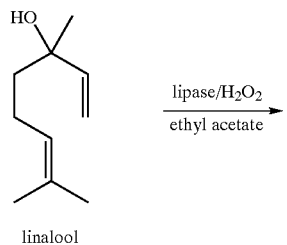

linalool

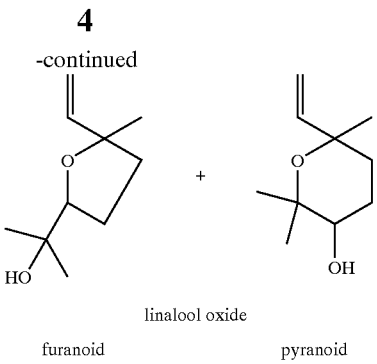

linalool oxide furanoid      pyranoid

Surprisingly, it is possible, with the process according to the present invention described, to prepare linalool oxide, which can be categorized as natural and therefore, can be used to produce natural aromas. In addition, it has surprisingly emerged that natural linalool oxide can be produced in yields of more than 90% in a straight-forward manner. This means that the process according to the present invention displays a considerable advantage compared with previously disclosed fermentation processes which operate with the aid of microorganisms, and is accordingly suitable for the industrial production of natural linalool oxide.

The linalool oxide can be used according to the present invention directly or in aromas for a wide variety of foodstuffs. This is possible in particular where it is intended to produce "citrus", "apricot" and "blueberry" flavors.

EXAMPLE

TABLE 1

| Item | Quantity | Starting material |
|------|----------|-------------------|
| 1 | 100.0 ml | Ethyl acetate, nat. |
| 2 | 7.7 g | Linalool, nat. |
| 3 | 6.0 ml | Hydrogen peroxide, ($H_2O_2$, 30%) |
| 4 | 0.1 g (245 units) | Lipase Chirazym C2 L2 (Roche Diagnostics) or Novozym 435 (Novo Nordisk) |

Procedure

Ethyl acetate (Item 1) is introduced into a 2 l three-necked flask with paddle stirrer, and linalool (Item 2), hydrogen peroxide ($H_2O_2$, 30% strength, Item 3) and enzyme (Item 4) are added while stirring slowly. The mixture is stirred slowly (about 100–120 rpm) at room temperature. The process is accompanied by analysis of the composition by GC every 1–2 days.

Result

With the GC results listed in Table 2, the percentage areas for acetic acid were calculated (except in the case of acetic acid).

TABLE 2

|  | Linalool (GC-%) | Linalool oxide F, trans and cis (GC-%) | Linalool oxide P, trans and cis (GC-%) | Linalool oxide-epoxide (GC-%) | Acetic acid (GC-%) |
| --- | --- | --- | --- | --- | --- |
| Precursor | 99.3 | — | — | — | — |
| 1 day | 5.1 | 32.9 | 4.2 | 57.1 | 19.7 |
| 2 days | 0 | 56.5 | 6.5 | 36.3 | 22.1 |
| 5 days | 0 | 79.8 | 9.1 | 9.0 | 24.2 |
| 7 days | 0 | 83.3 | 9.6 | 5.6 | 25.4 |

F: furanoid
P: pyranoid

The total yield of furanoid and pyranoid linalool oxide is about 93%.

Purification by distillation (10-plate column) of the linalool oxide-containing organic phase results in a product with a purity of 99% (GC) furanoid linalool oxide. This is organoleptically comparable in taste and odor with the nature-identical standard.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of linalool oxide or linalool oxide-containing mixtures comprising contacting:
    a) linalool or a linalool-containing mixture,
    b) lipase from microorganisms,
    c) hydrogen peroxide, and
    d) a carboxylic acid or a carboxylic ester, to form a reaction medium.

2. A process according to claim 1, wherein the linalool is D-linalool, L-linalool or essential oils containing D-linalool or L-linalool, or mixtures of these substances.

3. A process according to claim 1, wherein said microorganisms are selected from the group consisting of *Candida antarctica* strains, Pseudomonas sp., Humicola sp., *Mucor miehi*, or mixed cultures containing these microorganisms.

4. A process according to claim 3, wherein said yeast is *Candida antarctica*.

5. A process according to claim 1, wherein the hydrogen peroxide is at a concentration of from 0.1 to 80% to the reaction medium.

6. A process according to claim 1, wherein said carboxylic acid or carboxylic ester is ethyl acetate or acetic acid.

7. A process according to claim 1, wherein the lipase is from *Candida antarctica* strains, Pseudomonas sp., Humicola sp., *Mucor miehi*, or mixed cultures containing these microorganisms.

* * * * *